(12) United States Patent
Sigmon et al.

(10) Patent No.: US 10,172,588 B1
(45) Date of Patent: Jan. 8, 2019

(54) ULTRASOUND GUIDANCE SYSTEM AND METHOD

(71) Applicants: Carter Harrison Sigmon, San Diego, CA (US); Jeremy Hackworth, San Diego, CA (US); Bonnie S. Schnitta, East Hampton, NY (US)

(72) Inventors: Carter Harrison Sigmon, San Diego, CA (US); Jeremy Hackworth, San Diego, CA (US); Bonnie S. Schnitta, East Hampton, NY (US)

( * ) Notice: Subject to any disclaimer, the term of this patent is extended or adjusted under 35 U.S.C. 154(b) by 271 days.

(21) Appl. No.: 15/148,946

(22) Filed: May 6, 2016

Related U.S. Application Data

(60) Provisional application No. 62/157,821, filed on May 6, 2015.

(51) Int. Cl.
*A61B 8/14* (2006.01)
*A61B 8/08* (2006.01)
*A61B 8/00* (2006.01)
*A61M 5/32* (2006.01)

(52) U.S. Cl.
CPC .......... *A61B 8/0841* (2013.01); *A61B 8/4483* (2013.01); *A61B 8/461* (2013.01); *A61B 8/488* (2013.01); *A61B 8/5207* (2013.01); *A61B 8/54* (2013.01); *A61M 5/32* (2013.01)

(58) Field of Classification Search
CPC ..... A61B 8/0841; A61B 8/488; A61B 8/5207; A61B 8/54; A61B 8/461; A61B 8/4483; A61M 5/32
USPC .................................. 600/437–469
See application file for complete search history.

(56) References Cited

U.S. PATENT DOCUMENTS 6,053,871 A * 4/2000 Cockburn ............ A61B 8/0833
  600/459
6,336,899 B1 * 1/2002 Yamazaki ............ A61B 8/0833
  128/916

* cited by examiner

*Primary Examiner* — Sanjay Cattungal
(74) *Attorney, Agent, or Firm* — John F. Vodopia

(57) ABSTRACT

An ultrasound flashlight (USFL) configured to present an ultrasound image of a needle inserted in an animal body to deliver a treatment solution to a target structure location, where the image is used to guide a practitioner's positioning a delivery end of the needle. The ultrasound flashlight (USFL) includes a needle with a delivery opening for delivering the treatment solution and an access end opposite the delivery end. An insert is inserted in a lumen extending along a longitudinal axis of the needle housing between the access end and the delivery opening. The insert includes piezoelectric elements that are aligned in the lumen at communication ports in the needle housing, which ports are configured to pass ultrasound energy from inside to outside without passing the treatment solution. The energy from the elements is presented in a display image.

20 Claims, 11 Drawing Sheets

2-D IMAGE

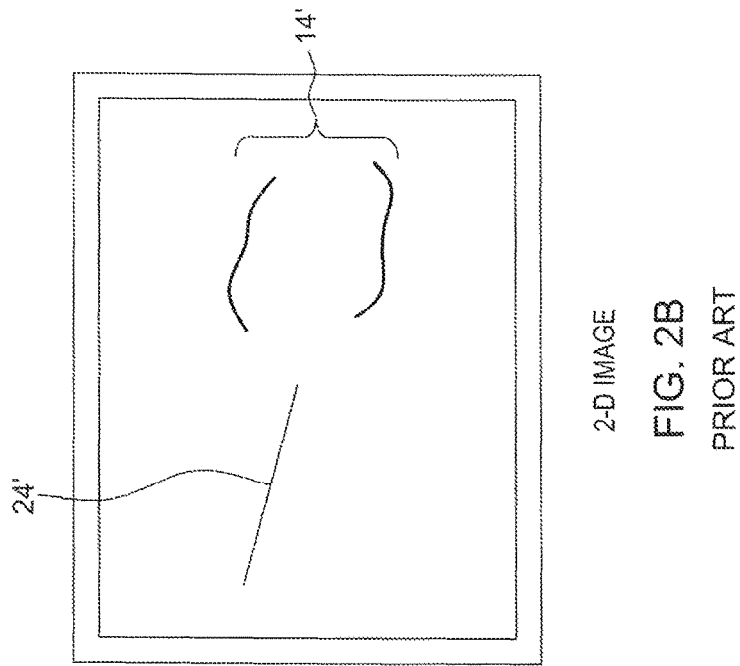
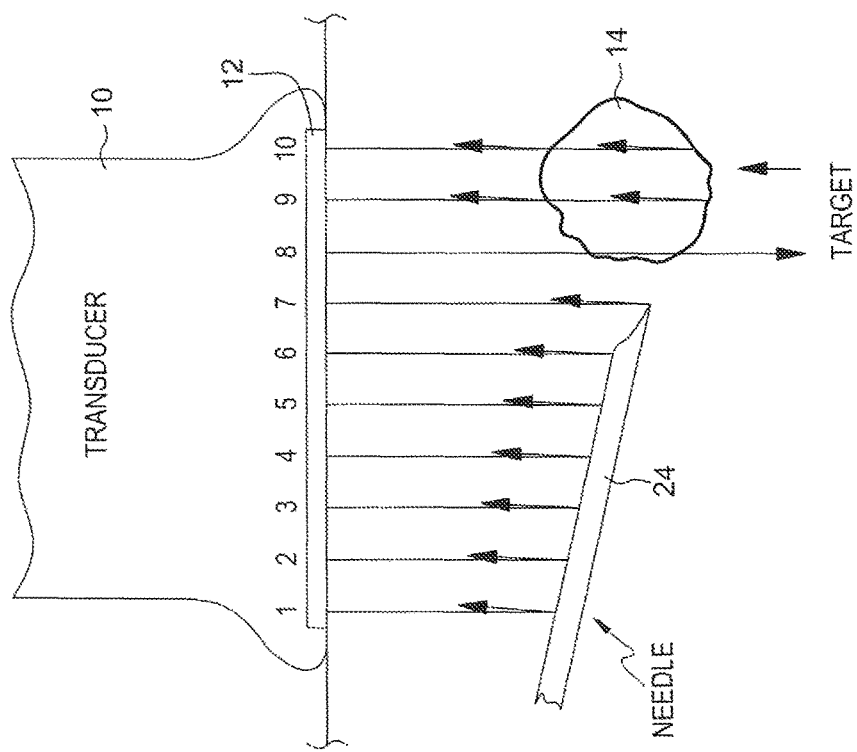

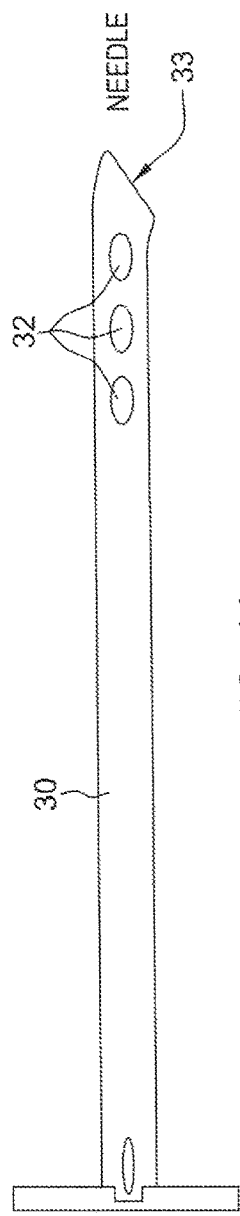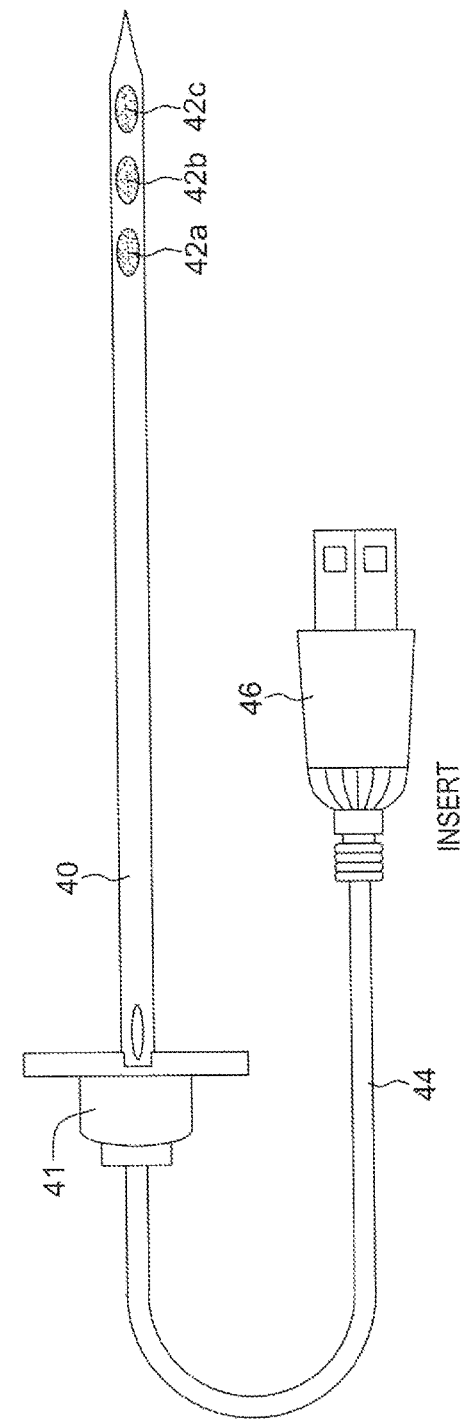

"OUT-OF-PLANE"
TOP DOWN VIEW

ULTRASOUND GUIDANCE SYSTEM AND METHOD

CROSS-REFERENCE TO RELATED APPLICATIONS

This application derives the benefit of the filing date of U.S. Provisional Patent Application No. 62/157,821, filed May 6, 2015, the content of which provisional application is incorporated herein by reference.

BACKGROUND OF INVENTION

The present invention broadly relates to needle localization, for example, insertion of a tip of a hypodermic needle to a required location in an animal such as a human being under treatment and, more particularly relates to a needle configured to be accurately guided using ultrasound, an ultrasound imaging system including the needle and method of guiding the needle using the ultrasound imaging system.

Ultrasound is used with increasing frequency to image body parts both to obtain diagnostic information, as well as an adjunct to help guide needle placement for a variety of reasons. For example, ultrasound is often used to help guide a needle tip to an area to deposit medication. The area of interest where the needle tip will traverse or ultimately lie is often around important vascular and nervous tissue that could easily be damaged or disrupted should the needle tip inadvertently pierce the structure. Because of this and several other reasons, it is imperative that the operator know the exact location of the needle tip at all times. However, with current ultrasound imaging systems and technology, visualizing the needle tip at all times is difficult and problematic.

An ultrasound machine or system that can be used to visualize tissue includes a transducer that contains an array of piezo-electrical crystals. As a pulsed current is applied to the piezoelectric crystals, pulsed ultrasonic phonons (packet of sound in the ultrasonic frequency) are generated that radiate from the transducer face and travel through the medium of interest. In this way, the ultrasound transducer operates as a transmitter. The ultrasound transducer also operates as a receiver to receive transmitted ultrasound energy reflected back by the different parts of medium of interest. A piezoelectric crystal (with similar characteristics to the transmitter piezoelectric crystal), that detects the sound energy produced by the transmitter responds to the energy by vibrating. The ultrasound transducer may include piezoelectric crystals dedicated to transmission and piezoelectric crystals dedicated to receiving, or may rely on the same piezoelectric crystals to both transmit and receive. In that case, after the crystals emit ultrasound energy in a transmission phase, there is a quiet or listening phase. That is, the ultrasound energy travels through the tissue and some of ultrasound energy is reflected (echo) off the tissue based on differences of tissue density and returns back to the "listening" crystals (pulse-echo cycle). As the crystals in the receive mode absorb the reflected, diffracted and/or diffused ultrasound energy, they vibrate creating a voltage or current signal with the magnitude that correlates to the strength of the returned reflected ultrasound energy. Using a signal processor (CPU), the return signals are processed and a two dimensional (2D) ultrasound image is rendered. Using a linear array of crystals and sweeping excitation pulse across this array to generate an array of transmitted ultrasound signals (FIG. 1A), linear spatial resolution can be determined. Using time delay and amplitude, the depth and contrast if the tissue medium is produced (FIG. 1B). With these pieces of information (see target and needle in FIG. 2A for a simple example of a reflected only signal), the CPU can convert the echoes (i.e., signal representative of the reflected ultrasound energy) into a 2D image that represents the tissue structures and a needle within the tissue (FIG. 2B).

Many of the structures that need to be accessed with a needle are such that the angle between transducer face and the needle is large, for example, greater than 30 degrees. With an increasing angle between the transducer face and needle (see FIG. 3), a decrease in the amount of reflected ultrasound energy is received or detected at the transducer making visualization very difficult. In addition, if the needle is below a strong reflecting surface, the needle becomes invisible.

SUMMARY OF THE INVENTION

The present invention overcomes the shortcomings of known arts, such as those mentioned above. For example, the invention provides a simple solution to needle visualization during ultrasound guided procedures that require needle guidance.

In one embodiment, the invention provides what is referred to as an ultrasound flashlight (USFL), which comprises a disposable needle with at least one and preferably three or more side ports or sealed eyelets, in addition to the delivery opening. The side ports or eyelets are filled with a lens or coating that allows for the transmission of ultrasound energy therethrough, while preventing treatment solution in the needle to pass out of the side ports or eyelets. The terms or phrases "side ports," "ports," "openings," "communication openings," and "eyelets" are used interchangeably herein to describe the sealed communication ports in the insert that allow for transmission of the ultrasound energy (for the insert) through the needle. A very thin, ultrasound transceiver (ultrasound insert as shown in the figures) is configured for insertion into the disposable needle. The ultrasound insert includes at least one and preferably 3 or more separate piezoelectric crystal elements that align with the corresponding at least one and preferably 3 or more side ports or eyelets in the disposable needle. The ultrasound insert may include control electronics that are controlled to generate signals to drive the piezoelectric elements to emit ultrasound signals through the (aligned) side ports or communication openings in the needle structure.

The electronics are preferably miniaturized and packaged in a small module mounted on or integral with an end portion (i.e., a handle of the insert). The ultrasound insert is connected by wire, bus or other means for communicating to the driving electronics. For example, a wireless receiver may be included in the handle which receives the control signals. In one form, the electrical signals for driving the piezoelectric elements in the insert are communicated from a controller (a microprocessor or microcontroller) connected to the insert through a wire, bus or wirelessly to the insert receiver.

Alternatively, the insert and the piezoelectric elements therein may be directly connected through the handle to a microcontroller device that generates the control signals for controlling the piezoelectric elements. The controller, whether it is part of the insert itself or a separate controller, such as in a control device or even part of an ultrasound imaging system with which the insert is used, includes a set of computer readable instructions that when processed, generate the signals to drive the elements. The instructions can be memory stored and downloaded either wirelessly or through a USB connection.

An ultrasound transducer or probe captures images of the needle (with the insert) and the ultrasound energy emitted by the insert when the needle and insert are moved into the animal body during a procedure, for example, a delivery of a treatment solution to a targeted structure. The ultrasound imaging system processes the energy received by the probe or transducer and reconstruct images for display on either a display of the ultrasound imaging system or a separate display.

Instead of two distinct phases found with traditional ultrasound machines (emitting and listening), the inventive ultrasound imaging system (i.e., USFL) typically operates with the inventive needle and ultrasound insert to operate with 4 phases: 1. Transducer or probe emitting phase for tissue and needle visualization; 2. Transducer or probe listening for tissue imaging; 3. Ultrasound emission from the piezo-electric elements in the insert to the needle (either by excitation of the elements in the ultrasound insert in response to the ultrasound energy transmitted by the transducer (passive) or in response to a signal generated by the CPU to actively drive the piezo-electric elements in the insert within the needle; and 4. Transducer or probe listening for ultrasound energy generated by the excited piezoelectric elements in the insert, which is inserted and present within the needle.

Phases 1 and 2 will be unchanged from standard ultrasound techniques. Depending on the application phases 3 and 4 are either used to further refine the information on the position of the object(s) to be imaged from the position of the piezo-electric crystal elements in the needle and ultrasound insert, or as an alternative. This information is then processed using software that implements various mathematical algorithms that take advantage of the special characteristics of the mathematical content of the additional time delay information to provide a precision localization of the object of concern, i.e., the disposable needle. This can also be used to image an object behind an object. Of course, the USFL need not operate at the same frequency as the imaging transducer, but for ease of description, we will assume that is the case.

Ultrasound imaging is limited by the physical properties of ultrasound interaction with tissue. Higher resolution of an ultrasound image requires a higher frequency. However, higher frequency energy is absorbed at a higher rate and thus penetration into deeper tissues is difficult as the emitted phonons loose energy quickly and are unable to reach deeper structures. Lower frequency ultrasound energy is able to penetrate deeper tissues, but resolution suffers and image quality is degraded.

In view of the fact that this inventive ultrasound based needle localization technique is using time delay as part of its method to determine location only, lower frequencies can be used, thus making localization at larger depths possible. This resolves the failures of a single piezoelectric element. That is, it is not only forward looking, but facilitates multidimensional imaging. Additionally, the use of more than one frequency will further facilitate the precision of the imaging. In greater detail, a certain amount of transmitted ultrasound signal energy is lost in tissue as a function of the distance, where the higher the frequency the higher the loss. This is unfortunate as the higher the frequency, the higher the quality of the rendered ultrasound image. By including a second source and method of ultrasound energy by way of the inventive needle/insert, conventional loss as a function of tissue depth is compensated for, and delivery of drugs or other substances through the needle (around the insert) is far more accurately affected than is possible using a traditional needle-guided ultrasound.

In an embodiment, the invention provides an ultrasound flashlight (USFL) configured to generate and present an ultrasound image of a needle inserted in an animal body to deliver a treatment solution to a target structure location, where the image may be relied upon as a guide for supporting a practitioner's positioning a delivery end of the needle at the target structure location in the animal body.

The ultrasound flashlight includes a needle comprising a housing including a delivery end formed with a delivery opening for delivering the treatment solution, an access end opposite the delivery end, a lumen extending along a longitudinal axis of the needle housing between the access end and the delivery opening and one or more communication ports in the housing configured to pass ultrasound energy from inside the lumen to outside the lumen without passing the treatment solution and an insert having a first end and a second end disposed substantially opposite the first end along a longitudinal axis of the insert, where the insert includes one or more ultrasound piezoelectric elements arranged proximate the first end and a connector positioned at the second end for connecting the piezoelectric elements to a controller.

The insert is configured to be inserted into the needle so that each of the ultrasound piezoelectric elements aligns with a respective one of the communication ports of the needle so that ultrasound energy generated by the each of the ultrasound piezoelectric elements passes substantially unobstructed though one of the communication ports aligned therewith and the generated ultrasound energy from the piezoelectric elements is detected and processed using an ultrasound imaging system and displayed in an image that operates as the guide.

For that matter, the controller generates and provides a signal to drive each of the ultrasound piezoelectric elements that is different from a signal generated and provided to drive each other of the ultrasound piezoelectric elements, such that at least one of a frequency, a frequency content, an energy content and a transmission duration of ultrasound energy emitted from each of the ultrasound piezoelectric elements driven by a respective different signal is identifiably different. Preferably, the ultrasound energy emitted from each of the ultrasound piezoelectric elements is separately identifiable from each other of the ultrasound piezoelectric elements in the image that operates as the guide. The image that operates as the guide is displayed on a display device that is connected directly to the connector, wherein the controller is connected to an ultrasound probe that is used to generate said image and wherein the controller processes ultrasound energy received via the ultrasound probe to generate said image.

The controller may be attached to or integral with the insert, may be at a location that is remote from the insert or may be part of an ultrasound imaging system. The image that operates as the guide is displayed on a display device, and wherein the display device is part of the ultrasound imaging system. Moreover, the ultrasound energy emitted from each of the ultrasound piezoelectric elements that is presented in the image that operates as the guide is preferably separately identifiable from the ultrasound energy emitted from each other of the ultrasound piezoelectric elements and presented in the image that operates as the guide, thereby identifying a different location of each communication port of the needle in said image. The different locations of each communication port of the needle are identified by a different color in said image.

The invention also includes an ultrasound imaging system configured to generate and present an ultrasound image of a needle inserted in an animal body to deliver a treatment solution to a target structure location, where the image may be relied upon as a guide for supporting positioning a delivery end of the needle at the target structure location.

The ultrasound imaging system comprises an ultrasound wand or probe, a computer processor to which the ultrasound wand or probe is connected, a display device connected to the computer processor, a needle comprising a housing including a delivery end formed with a delivery opening for delivering the treatment solution, an access end opposite the delivery end, a lumen extending along a longitudinal axis of the needle housing between the access end and the delivery opening and one or more communication ports in the housing configured to pass ultrasound energy from inside the lumen to outside the lumen without passing the treatment solution and an insert having a first end and a second end disposed substantially opposite the first end along a longitudinal axis of the insert, where the insert includes one or more ultrasound piezoelectric elements arranged proximate the first end and a connector positioned at the second end for connecting the piezoelectric elements to the computer processor.

The insert is configured to be inserted into the needle so that each of the ultrasound piezoelectric elements aligns with a respective one of the communication ports of the needle so that ultrasound energy generated by the each of the ultrasound piezoelectric elements passes substantially unobstructed though one of the communication ports aligned therewith and the generated ultrasound energy from the piezoelectric elements is detected by the ultrasound probe or wand, processed by the computer processor and displayed on the display device in an image that operates as the guide.

The ultrasound imaging system may further comprise a memory for storing computer code for generating signals used to drive the ultrasound piezoelectric elements, for controlling the ultrasound energy transmitted from the wand or probe in a transmit mode and for processing ultrasound energy received by the wand or probe in receive mode. In a variation, the display device is positioned in the wand or probe. Moreover, the computer processor may be positioned in the wand or probe.

In another embodiment, the invention provides an ultrasound-based method for guiding a needle and insert combination in an animal body to deliver a treatment solution to a target structure location, wherein the needle comprises a housing with a delivery end formed with a delivery opening, an access end opposite the delivery end, a lumen extending along a longitudinal axis of the needle housing between the access end and the delivery opening and one or more communication ports in the housing configured to pass ultrasound energy from inside the lumen to outside the lumen without passing the treatment solution and wherein the insert comprises a first end and a second end disposed substantially opposite the first end along a longitudinal axis of the insert, one or more ultrasound piezoelectric elements arranged proximate the first end and a connector positioned at the second end for connecting the piezoelectric elements to control electronics.

The method includes first inserting the insert into the needle so that the one or more ultrasound piezoelectric elements are aligned with the one or more communication ports in the needle, second inserting the needle and insert combination into the animal body, operating the controller to generate and provide an electrical signal to each ultrasound piezoelectric element within the insert to generate and emit the ultrasound energy through the communication ports in the needle, operating an ultrasound transducer or probe to receive at least the ultrasound energy emitted from the communication ports in the needle, processing the received ultrasound energy and generating a display image that identifies a location of the needle and insert combination, a location of the target structure and a location of the communication ports and guiding the needle and insert combination to the target structure in reliance upon the generated display image.

Preferably, the step of processing the received ultrasound energy and generating the display image identifies the location of the communication ports using a different color for each target port location. The step of processing the received ultrasound energy and generating the display image may alternatively identify the location of the communication ports using a different color for each communication port location. Preferably, the insert includes an ultrasound piezoelectric element at a tip end, and wherein the step of first inserting includes aligning the ultrasound piezoelectric element at the tip end with the delivery opening in the delivery end of the needle so that signal energy that is generated by said tip end ultrasound piezoelectric element is emitted out of the delivery end in a direction substantially aligned with the longitudinal axis of the insert and, the step of guiding includes generating and communicating a signal to the practitioner when the delivery end of needle and insert combination arrives at the target structure, in reliance upon the received ultrasound energy emitted from the delivery end thereof. For that matter, wherein the target structure may be a fetus or a tumor to which the treatment fluid is delivered in any of the embodiments of the invention.

BRIEF DESCRIPTION OF THE DRAWINGS

Further features and advantages of the invention will become apparent from the description of embodiments that follows, with reference to the attached figures, wherein:

FIG. 2A depicts the conventional ultrasound transducer (of FIG. 1A) with a needle proximate the anatomical object or target;

FIG. 2B depicts a representative 2D image of the anatomical structure or target and needle, derived by a conventional ultrasound imaging system; that represents the tissue structures and the needle within the tissue.

FIG. 4A depicts an exemplary embodiment of a disposable needle or stub in accordance with the invention;

FIG. 4B depicts an exemplary embodiment of a disposable ultrasound insert configured to be inserted into the needle of FIG. 4A;

DETAILED DESCRIPTION OF THE INVENTION

The following is a detailed description of example embodiments of the invention depicted in the accompanying drawings. The example embodiments are presented in such detail as to clearly communicate the invention and are designed to make such embodiments obvious to a person of ordinary skill in the art.

Figure 1B:
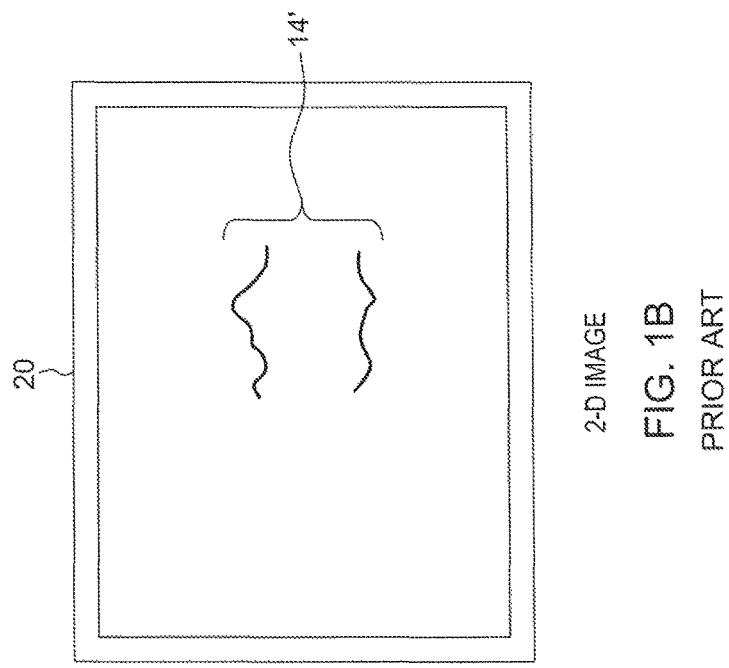
FIG. 1B depicts a representative 2D image derived by a conventional ultrasound imaging system, for example, that may be attached to the ultrasound transducer depicted in FIG. 1A.
Figure 1A:
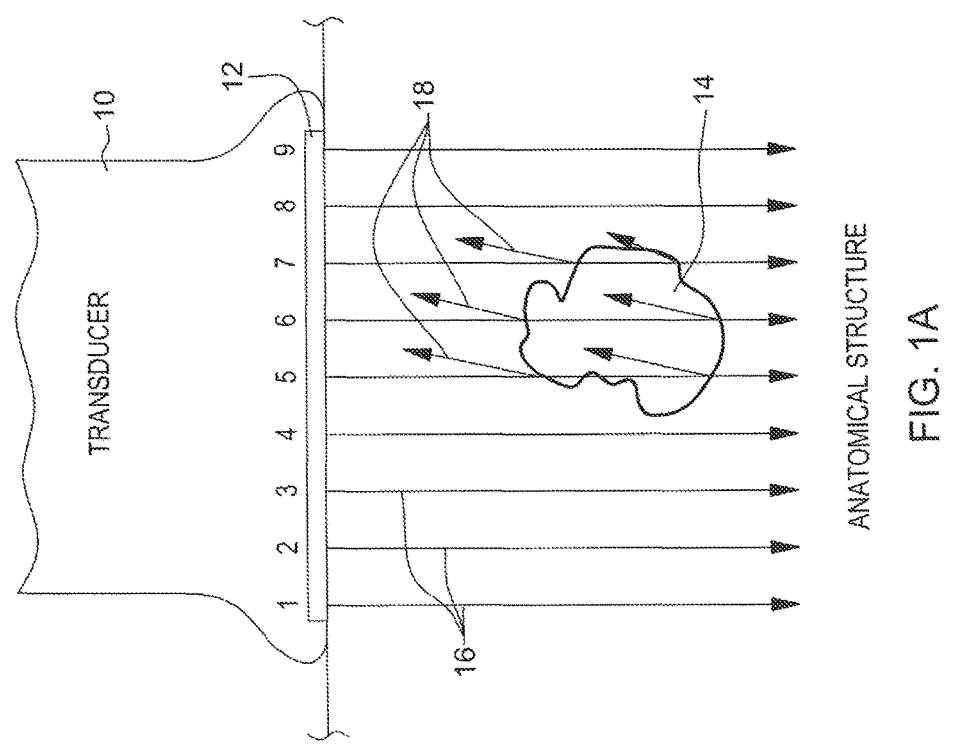
FIG. 1A depicts a conventional ultrasound transducer and an anatomical structure or target to be imaged by an ultrasound imaging system to which the transducer is connected.

FIG. 1A depicts a transducer 10 comprising a one-dimensional (1D) array of piezo-electric crystal elements 12, including an anatomical structure 14 in the path of directional arrows 16 representative of the path taken by the energy transmitted by each crystal. Arrows 18 are representative of the return energy reflected back from the anatomical structure 14. FIG. 1B depicts a representative 2D image 14' derived by processing the return signals detected by the transducer.

FIG. 2A depicts a transducer 10 such as that depicted in FIG. 1, with a conventional needle 24 proximate the anatomical structure or target 14, to highlight that a part of transmitted ultrasound energy is reflected from both the needle 24 (based on its position relative the transducer 10, as will be explained in further detail below) and the target structure. FIG. 2B depicts a 2D image 14' that represents the tissue structures and the needle 24' within the tissue.

Figure 3:
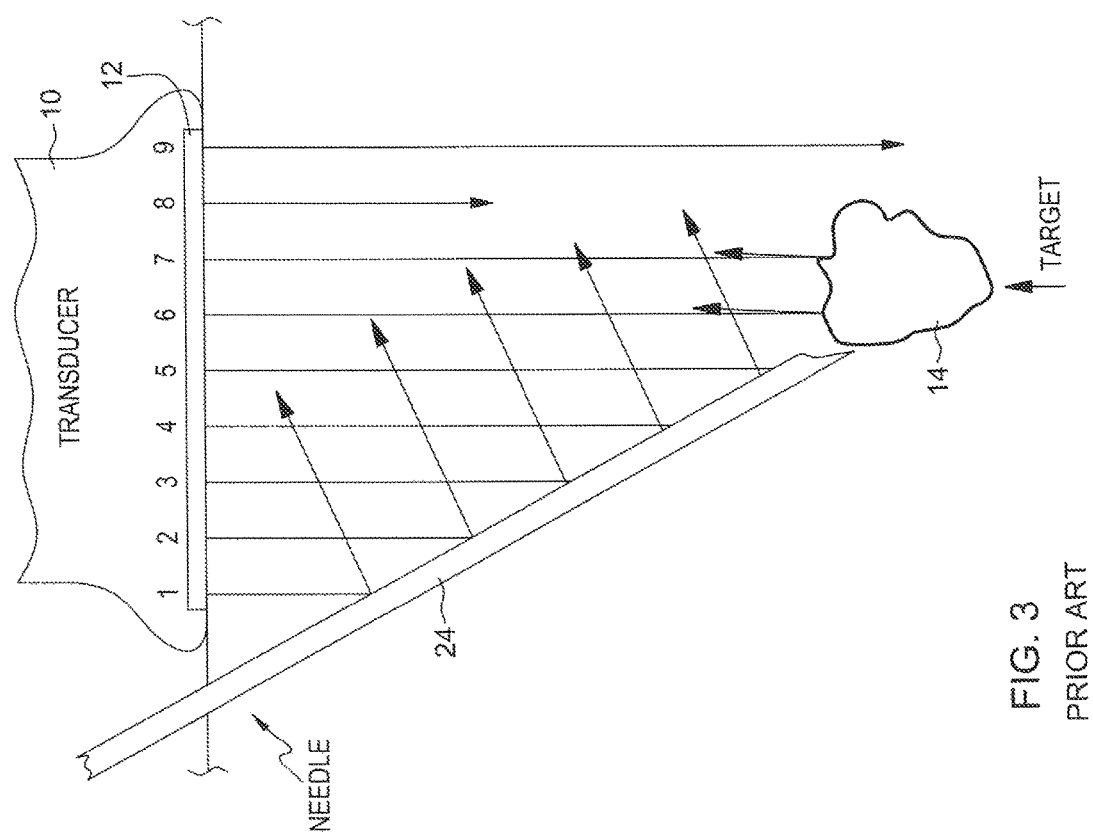
FIG. 3 depicts the conventional ultrasound transducer (of FIGS. 1A and 1B), the anatomical object or target and the needle proximate the anatomical object or target.

FIG. 3 depicts the transducer 10, the needle 24 and the target structure 14 wherein the needle 24 is at an angle that makes it problematic for the ultrasound energy reflected (or a sufficient amount thereof) from the needle 24 to be received or effectively detected by the ultrasound transducer in receive mode and, therefore, imaged; that is, in the arrangement as shown, an image of the needle is unlikely to be effectively reconstructed because the reflected or echoed ultrasound energy will not reach the transducer secondary to the steep angle of the needle.

FIG. 4A depicts an exemplary embodiment of a disposable needle or stub portion 30 of the needle and insert combination of the invention ("needle"). The needle 30 as shown is shaped much like a Tuohy-type needle, which includes a curved end with an opening for delivery of treatment fluid, but modified to include one or more eyelets or communication ports 32 (3 in the embodiment shown). The eyelets or communication ports correspond and line up with one or more piezoelectric elements 42 (3 in the embodiment shown, e.g., 42a, 42b and 42c) of an ultrasound insert 40 (FIG. 4B). FIG. 4B depicts an exemplary embodiment of a disposable ultrasound insert 40 configured to be inserted into the FIG. 4A needle 30. Insert 40 is configured to be inserted into and used in combination with the needle 30. The side ports or openings 32 in the needle 30 are filled with a lens or coating (transparent in FIG. 4B) that allows for the transmission of ultrasound energy from the aligned piezoelectric elements 42a, 42b, and 42c in the insert 42 therethrough, while preventing treatment solution in the needle 30 to pass out of the side ports or openings.

The insert 40 includes a handle portion 41 and electronics required for operation of the piezoelectric elements, or a transducer array of piezoelectric elements. The handle portion 41 preferably includes one or more activators for activating the one or more piezoelectric elements 42. A cable or wire 44 is shown connected to the handle 41 on one side and to a connector 46 on another side of the wire. The connector may be plugged into an AC outlet, or a DC power supply. The connector as shown includes a converter to convert the AC from the outlet to a proper voltage and current to drive the electronics and the elements 40. Preferably, the connector also provides a USB or like connection to a separate microcontroller or microprocessor (not shown) for controlling the element operation, e.g., a beamformer. Alternatively, a controller may be included in the connector 46 or handle 41 with an associated memory and/or wireless transceiver (not shown) for communicating with the controller thereat.

Figure 5A:
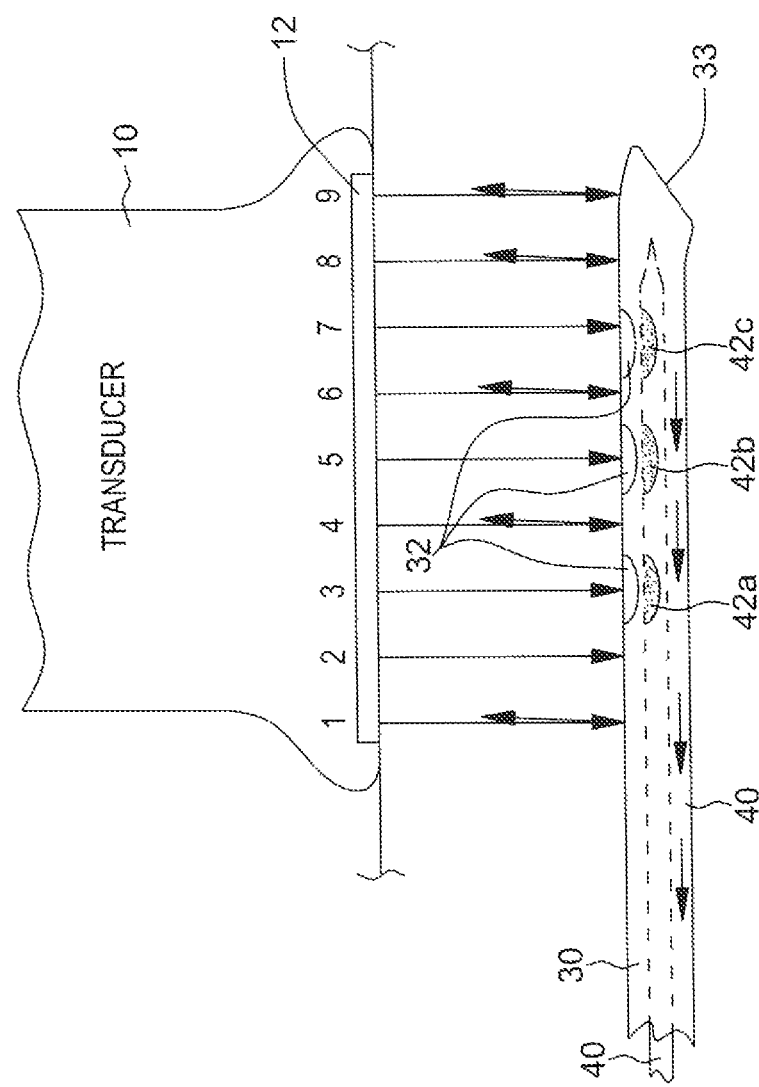
FIG. 5A shows a transducer transmitting u/s energy to a needle (FIG. 4A) inserted in a patient, where the needle include the inventive insert depicted in FIG. 4B, to highlight that less energy is reflected from the holes in the needle than surface of needle during transducer operation.

FIG. 5A shows a transducer 10 with an array 12 of nine (9) piezoelectric elements and a needle 30 with an ultrasound insert 30 inserted therein. The needle 30 comprises three (3) piezoelectric elements 42a, 42b and 42c arranged at three (3) respective ports or communication openings 32 in the needle 30. The insert 40 is positioned in the needle 30 (as shown) so that its longitudinal axis is substantially aligned with the longitudinal axis of the needle, and so that the piezoelectric elements in the insert are positioned opposite the communication openings or ports 32. The material used to fill the physical breaks in the needle material at the communication openings or ports 32 not only seals the openings or ports but preferably is chosen to facilitate or enhance transmission of ultrasound energy therethrough. One or more of the three (3) piezoelectric elements 42a, 42b, 42c in the needle/insert 30/40 combination are controlled by the handle electronics or by software running in a controller in the handle or another location (not shown in FIG. 5A) to emit a series of single or multiple-frequency pulses of ultrasound energy (in transmit mode); the energy is reflected from the needle/insert 30/40 combination. The reflected energy reaches and is detected by the piezoelectric crystal elements in array 12 of the transducer or probe 10 (in receive mode), as shown. Processing the ultrasound energy received at the piezoelectric elements in the transducer array 12 realizes additional positional information of each eyelet or communication port 32 and piezoelectric element 42a, 42b, 42c positioned thereat. That is, the energy that is emitted at the needle exits (from elements 42a, 42b, 42c) it is detected different from the energy transmitted from the transducer in transmit mode and reflected from the needle housing.

Figure 5C:
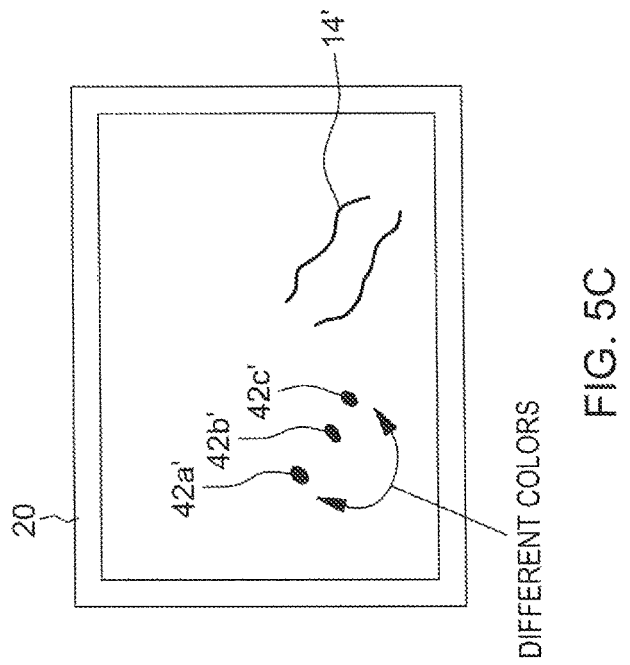
FIG. 5C depicts an image that is displayed on a display device highlighting a position of the energy received from the three piezoelectric elements in the needle insert, relative an image of the target derived from energy transmitted from the array 12 (not expressly shown). Using color to distinguish the locations is helpful to clearly communicate the information.
Figure 5B:
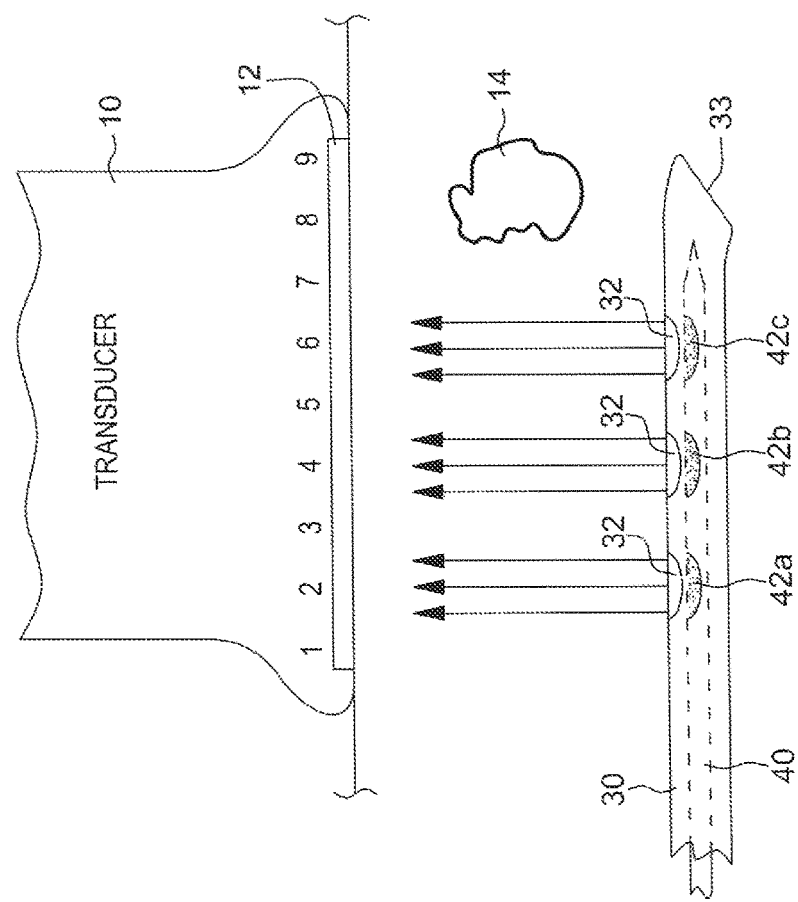
FIG. 5B highlights a state where the transducer is "listening" to the ultrasound energy transmitted from the piezoelectric elements in the insert, through the openings or holes in the needle.

FIG. 5B highlights the transducer 10 "listening" to the ultrasound energy transmitted from the three (3) piezoelectric elements 42a, 42b, 42c in the needle/insert 30/40 combination. This ultrasound energy, in addition to the ultrasound energy received from the conventional transmit/receive cycle of the transducer or probe 10, will reinforce positional information of the individual side ports 32 in the needle 30. Preferably, the ultrasound energy signal emitted by the needle/insert 30/40 combination is detectably different that the ultrasound signal emitted from the transducer or probe 10. For example, the energies may be transmitted as different frequencies, durations, shapes, lengths, etc. The skilled artisan should recognize that the exemplary embodiment(s) shown are for information purposes only and are not meant to limit the scope of the invention in any way. For example, the number of piezoelectric elements in the transducer 10 and/or the needle/insert 30/40 combination may be modified, particularly in the needle/insert combination, without deviating from the scope of the invention.

FIG. 5C depicts an image comprising three image portions 42a', 42b', 42c', that is displayed on a display device 20 of an ultrasound imaging system to which the transducer or probe 10 is connected. Image portions 42a', 42b', 42c' highlight a position of the energy received from the three piezoelectric elements 42a, 42b, 42c in the needle insert 40 (in needle 30), relative an image 14' of the target structure 14. The image 14' of the target structure 14 is derived from energy transmitted and received from the array 12. The image portions 42a', 42b' and 42c' are can be displayed in different colors by the ultrasound imaging system so that the practitioner can readily correlate the position of the needle 30 containing the insert 40 with the 3 elements (42a, 42b, 42c), i.e., the needle 30 position information relative the target. For that matter, the energy received from the needle may be used as the only source.

Please note that while the piezoelectric elements are shown positioned sequentially along the longitudinal axes of the exemplary needle inserts depicted herein, and the corresponding side ports in the needle configured to operate with said needle inserts also are aligned in a sequential arrangement along the longitudinal axes of the needles, the invention is not limited to such an arrangement. For example, the piezoelectric elements in the insert and the corresponding side ports in the needle may be arranged at different radial locations along an annular ring on an outer surface of the insert, aligned with ports located at different radial locations in the structure of the needle, and variations thereon, without deviating from the scope and spirit of the invention. The sequential, radial or other geometric arrangements of the piezoelectric elements about the inert, and corresponding communication ports in the needle configured for use therewith, may be utilized without the use of the ultrasound transducer or probe, as long as the insert is driven in both transmit and receive mode. That is, in receive mode, the piezoelectric elements in the insert may not just transmit, but actually receive and process the energy to put up an image to support needle positioning a display device included in the insert handle, or connected to the insert handle, as long as the insert controller is programmed to do so.

Figure 6:
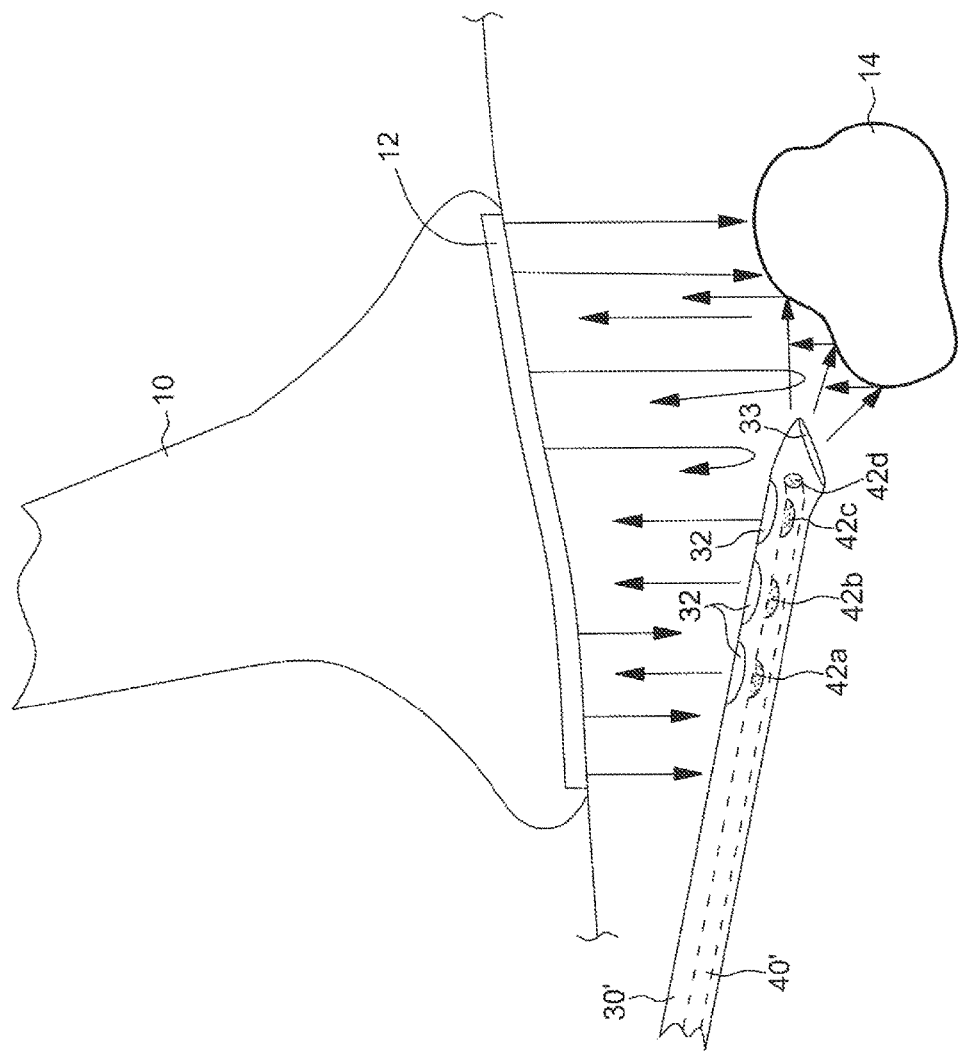
FIG. 6 depicts an alternative embodiment of the needle and insert depicted in FIGS. 4A, 4B, 5A, 5B and 5C, where an additional piezoelectric element is positioned at the tip of the insert in order to emit ultrasound signal energy out of the treatment liquid delivery opening in the tip of the needle.

FIG. 6 depicts an alternative embodiment of the needle/insert 30/40 depicted in FIGS. 4A, 4B, 5A, 5B and 5C, as the insert 40" of FIG. 6 includes an additional piezoelectric element 42d that is positioned proximate the delivery opening 33 at the tip of the needle 30' and when the insert 40' is inserted and properly aligned within the needle 30'. There is no need for the additional communication port in view of the fact that delivery port 33 already is present in the needle 30' and unobstructed. The ultrasound energy can be radiated from the additional piezoelectric element 42d in a direction aligned with the central longitudinal axis of the needle 30' (and the insert 40'), correlated to the needle heading. While the ultrasound signal emitted from the additional piezoelectric element 42d might be affected by any delivery fluid passing thereover at delivery, such fluid movement will occur after localization.

Figure 7A:
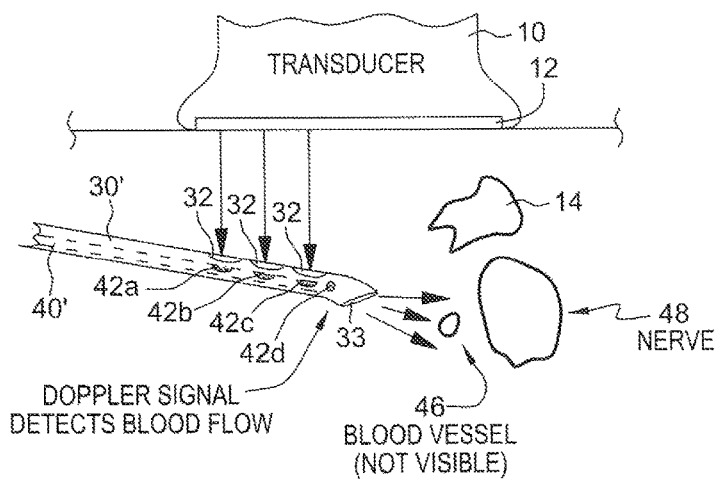
FIG. 7A depicts the needle and insert heading towards a target for a delivery where a vessel 46 and a nerve 48 are in front of the needle, proximate the target.
Figure 7B:
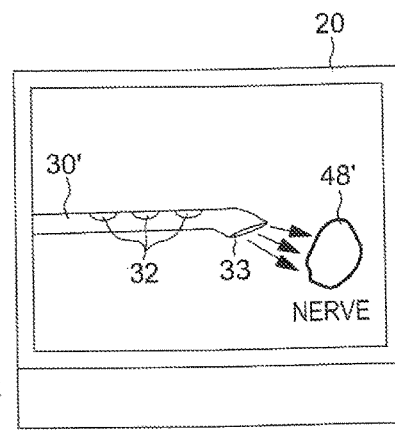
FIG. 7B is a display shot highlighting where the structure ahead of the needle and insert is unknown (not a blood vessel based on a Doppler analysis)
Figure 7C:
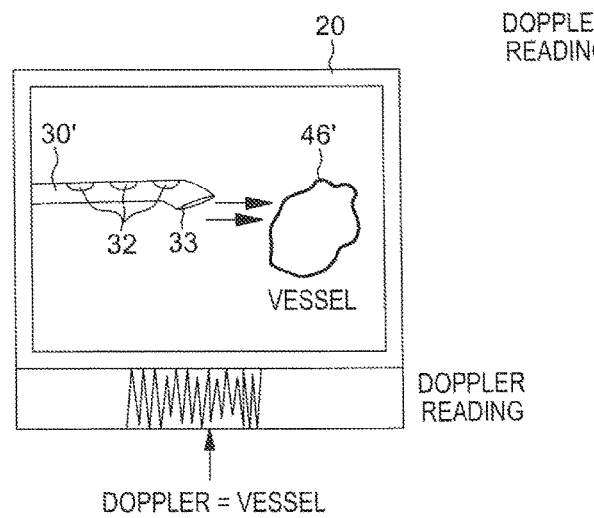
FIG. 7C is a display shot where the structure ahead of the needle and insert is a blood vessel, and is identified as such based on a Doppler analysis.

FIG. 7A depicts the needle/insert 307'/40' heading towards a target structure 14 for delivery of a treatment solution, where a blood vessel 46 and a nerve 48 are in front of the needle/insert, that is, in the needle/insert heading. The invention is advantageous in that the piezoelectric elements 42a, 42b, 42c in the ultrasound insert 40' are driven to generate Doppler signals that are received used by the transducer 10 and processed ultrasound imaging system connected thereto (not shown) to identify vessel position in reliance on the blood flow therein. FIG. 7B highlights the circumstances where the nerve structure 48 ahead of the needle/insert 30'/40' is unknown. Therefore, the practitioner can rely on the Doppler reading from the signal energy first transmitted by needle/insert 30'/40', which is detected and processed by the ultrasound imaging system, to identify if the structure is a vessel or not; as there is no Doppler signal generated by transmitted ultrasound, it can safely be assumed that the image 48' of the nerve structure depicted in the display image is not a blood vessel. FIG. 7C represents the display image 46' on display 20 that the user would see when the structure 46 is actually a blood vessel is in front of the needle/insert 30'/40'. As should be apparent, the additional ultrasound signals from the needle/insert 30'/40' enhance the processing ability of the ultrasound imaging system to guide the practitioner.

Figure 8A:
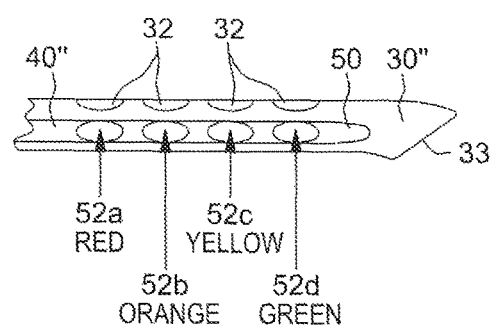
FIG. 8A shows another embodiment of a needle and insert, where the insert includes four (4) piezoelectric elements (that will be represented in any image as different colors, e.g., red, orange, yellow and green, respectively) and the needle includes four (4) openings corresponding to the insert elements.
Figure 8B:
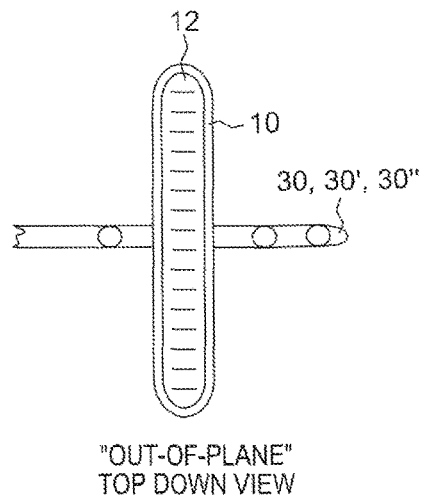
FIG. 8B highlights a case where the array of piezoelectric elements in the transducer is aligned in a direction that is substantially perpendicular to an axial length of the needle and insert to be inserted.
Figure 8C:
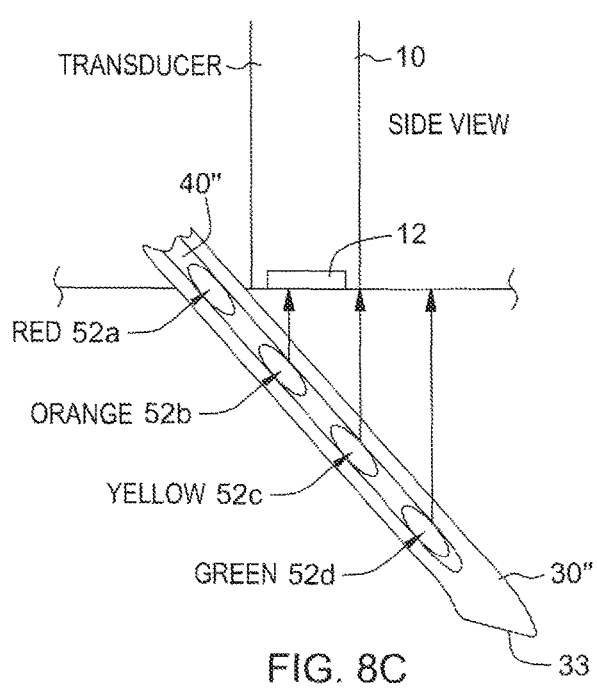
FIG. 8C further highlights a problem associated with the case presented in FIG. 8B, where ultrasound energy transmitted from three (3) of the four (4) piezoelectric elements in the insert and needle combination is unlikely received (referred to as an "out of plane" problem) at the transducer.

FIG. 8A shows an embodiment with four (4) piezoelectric elements 52a, 52b, 52c, 52d in the insert 40" and four (4) corresponding side ports or communication openings 32 in the needle 30. FIGS. 8B and 8C highlight a problem addressed by the invention, i.e., that the array of piezoelectric elements 12 in the transducer 10 and is at times aligned in a direction that is substantially perpendicular to the longitudinal axial of a needle to be inserted (in this case, needle/insert 30/40, 30'/40', 30"/40"), where but for the inventive operation, guidance in such an angular arrangement would be challenging to the practitioner.

The solution relies upon four (4) piezoelectric elements 52a, 52b, 52c, 52d that each are configured to generate individual ultrasound signals that are distinguishable from each other. In this way, when the signal energy received from these individual elements is processed by the ultrasound imaging system, the reconstructed image of same can be displayed to distinguish the respective sources. In the example shown, the different elements 52a, 52b, 52c, 52d are presented in the display in such a way that they are distinguishable. In one embodiment, the images of the energy derived from the 52a, 52b, 52c, 52d are represented as red, orange, yellow and green, respectively.

Figure 8D:
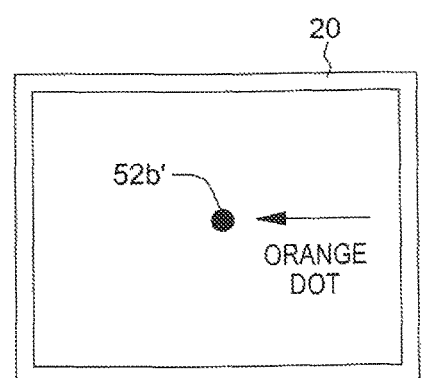
FIG. 8D presents an image rendered in cooperation with the transducer, where the one element in the insert transmitting in a position to be received is the element identified as orange.

In FIG. 8C, it should be clear that the ultrasound energy transmitted from three (3) of the four (4) piezoelectric elements (52a, 52c, 52d) in the needle/insert 30'/40" is unlikely to be received (referred to as an "out of plane" problem) by the array 12 in transducer or probe 10. Only energy from element 52b appears to be in range with any of the elements in the transducer array 12. FIG. 8D shows the image rendered by the ultrasound imaging system and transducer 10, where the one element transmitting in a position to be received (i.e., element 52b of needle/insert 30"/40" 3) is reconstructed as image 52b in display 20 as orange. By knowing which opening in needle 30" the energy represented as orange in the reconstructed image, the practitioner knows where the needle is in the animal body, and how to further move the needle/insert 30"/40" to navigate to the target structure (not shown in FIG. 8D and deliver the treatment solution. For that matter, different schemes or techniques may be implemented by the software that is operational in the ultrasound imaging system in order to guide the needle/insert to the exact location, such as signaling with sound or light, the frequency of which changes in proximity to the target.

Figure 9A:
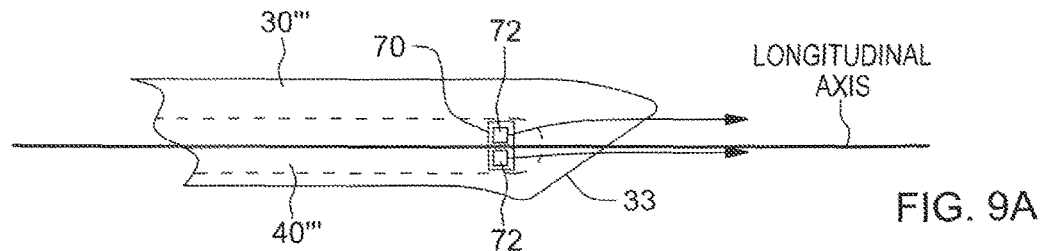
FIG. 9A depicts an embodiment of the needle and insert combination of the invention, where the insert includes a 1D array of one or more piezoelectric elements that is arranged in a forward position so that the piezoelectric elements transmit ultrasound energy in a direction aligned with the longitudinal axis of the needle/insert combination.

FIG. 9A depicts an embodiment of the needle 30'" and insert 40'" combination, where the insert 40'" includes a 1D array 70 of one or more piezoelectric elements 72 that is arranged in a forward position at the tip or delivery opening 33 in the needle 30'" so that the piezoelectric elements 72 transmit ultrasound energy in a direction aligned with the longitudinal axis of the needle/insert combination. Fig. B depicts an embodiment of the of a 1D array 70 comprising the piezoelectric elements 72 in the needle/insert combination of FIG. 9A, and highlight the shape of the beam formed thereby, which is in alignment with the longitudinal axis of the needle/insert combination.

Figure 9B:
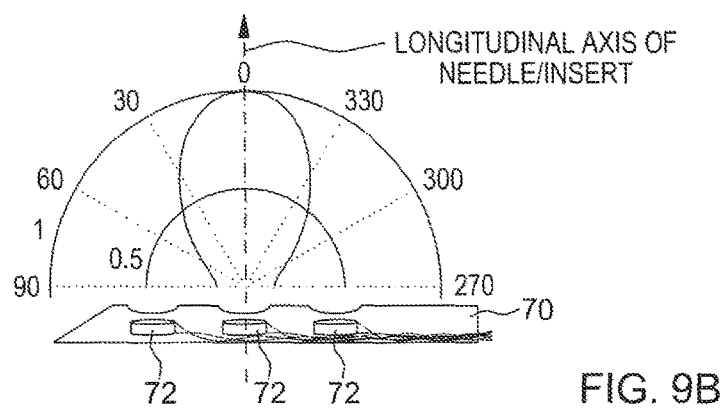
FIG. 9B depicts an embodiment of the of a 1D array comprising the piezoelectric elements in the needle/insert combination of FIG. 9A, and highlighting the shape to the beam formed thereby in alignment with the longitudinal axis of the needle/insert combination.
Figure 9C:
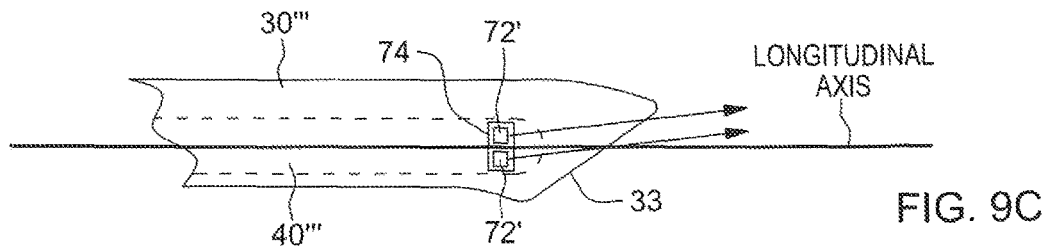
FIG. 9C depicts an embodiment of the needle and insert combination of the invention, where the insert includes a 1D array of one or more piezoelectric elements that is arranged in a forward position so that the piezoelectric elements transmit ultrasound energy in a direction that is offset at an oblique angle with the longitudinal axis of the needle/insert combination.
Figure 9D:
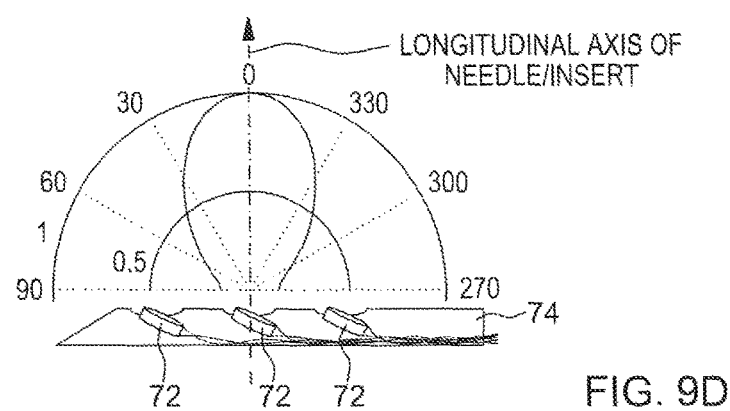
FIG. 9D depicts an embodiment of the of a 1D array comprising the piezoelectric elements in the needle/insert combination of FIG. 9C, and highlighting the shape to the beam formed thereby offset at the oblique angle with the longitudinal axis of the needle/insert combination.

FIG. 9C depicts an alternative embodiment of the needle and insert combination of FIGS. 9A, 9B the invention, where the insert 40'" includes a 1D array of one or more piezoelectric elements 72' that are arranged in a forward position to transmit ultrasound energy in a direction that is offset at an oblique angle with the longitudinal axis of the needle/insert combination. FIG. 9D depicts an embodiment of the of a 1D array 74 comprising the piezoelectric elements 72' in the needle/insert combination of FIG. 9C, and highlighting the shape to the beam formed thereby, which is offset at the oblique angle with the longitudinal axis of the needle/insert combination.

Figure 10A:
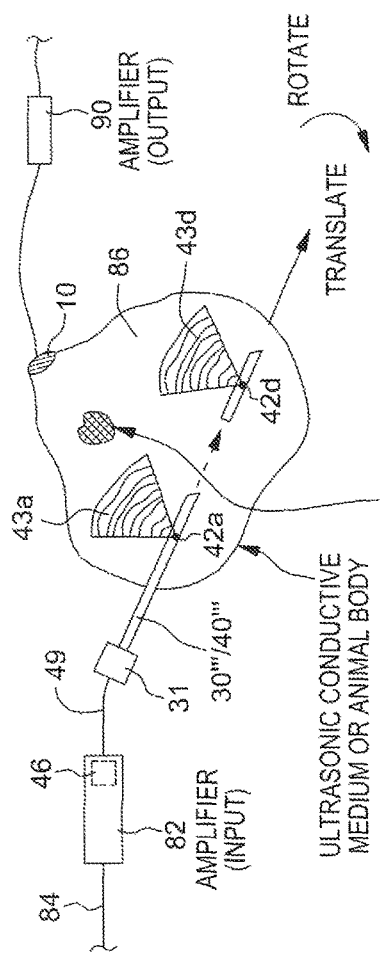
FIG. 10A depicts a system for operating any of the inventive needle/insert combinations.

FIG. 10A depicts a system for operating any of the inventive needle/insert combinations, for example, the needle/insert 30'"/40'" with handle 31. An input amplifier 82 connected to a bus 84 is controlled by a controller (not shown) to amplify signals for driving any of the elements 42 in the insert 40'", which emit ultrasound energy based thereon into the animal tissue 86 that includes the target structure 14. For example, the elements 42a and 42d are driven to emit energy patterns 43a and 43d, respectively, as shown, which is amplified by output amplifier 90, which may be part of an ultrasound imaging system (not shown) attached thereto.

Figure 10B:
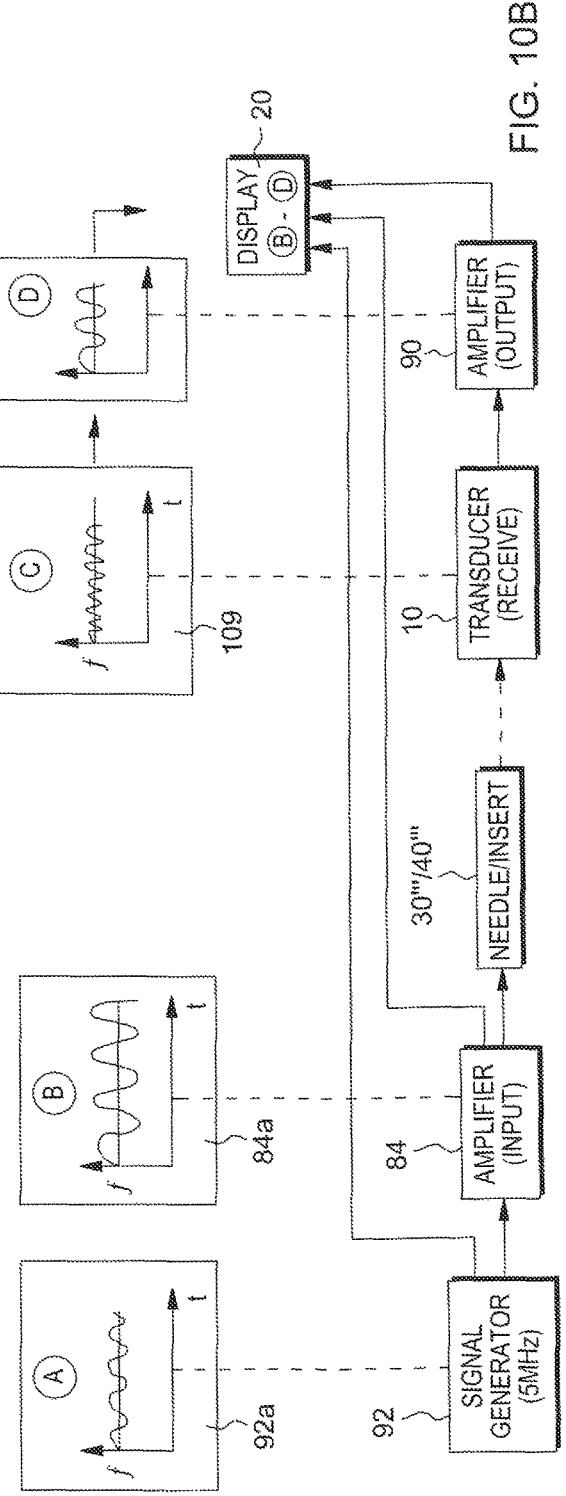
FIG. 10B identifies a signal generator 92 and a representative signal f(t) output thereby in a 2D representation 92a (act (A)).

FIG. 10B identifies a signal generator 92 and a representative signal f(t) output thereby in a 2d representation 92a (act (A)). The amplified signal af(t) is shown in a 2d representation 84a (act (B)), which is then provided to the needle/insert. For example, 5 MHz may be used. A signal received from the needle/transducer $f_r(t)$ is detected by transducer 10 (act (C)), which is amplified in amplifier 90 to realized amplified signal a $f_r(t)$ (act (D)). Additional signal processing can now be added to this system to make it the image clearer, or in the case of adaptive filtering the error function can trigger the existence of a found object.

The embodiment depicted in FIGS. 10A and 10B is presented to convey the ability of the system including the exemplary needle/insert 30'"/40'" whereby the separate elements 42a . . . 42d are driven by separate electrical signals to generate different ultrasound energy patterns. As explained above, such configuration may rely upon use of driving signals for each element that operate at different frequencies.

As will be evident to persons skilled in the art, the foregoing detailed description and figures are presented as examples of the invention, and that variations are contemplated that do not depart from the fair scope of the teachings and descriptions set forth in this disclosure. The foregoing is not intended to limit what has been invented, except to the extent that the following claims so limit that.

What is claimed is:

1. An ultrasound flashlight (USFL) configured to generate and present an ultrasound image of a needle inserted in an animal body to deliver a treatment solution to a target structure location, where the image may be relied upon as a guide for supporting a practitioner's positioning a delivery end of the needle at the target structure location in the animal body, the ultrasound flashlight comprising:

a needle comprising a housing including a delivery end formed with a delivery opening for delivering the treatment solution, an access end opposite the delivery end, a lumen extending along a longitudinal axis of the needle housing between the access end and the delivery opening and one or more communication ports in the housing configured to pass ultrasound energy from inside the lumen to outside the lumen without passing the treatment solution; and an insert having a first end and a second end disposed substantially opposite the first end along a longitudinal axis of the insert, where the insert includes one or more ultrasound piezoelectric elements arranged proximate the first end and a connector positioned at the second end for connecting the piezoelectric elements to a controller;

wherein the insert is configured to be inserted into the access end of the needle so that each of the ultrasound piezoelectric elements aligns with a respective one of the communication ports of the needle;

wherein during USFL operation, ultrasound energy generated by the each of the ultrasound piezoelectric elements passes substantially unobstructed though each one of the communication ports aligned therewith; and wherein the generated ultrasound energy from the piezoelectric elements that passes through the communication ports is detected and processed using an ultrasound imaging system and displayed in an image that operates as the guide for supporting the practitioner's positioning of the needle.

2. The ultrasound flashlight (USFL) of claim 1, wherein the controller generates and provides a signal to drive each of the ultrasound piezoelectric elements that is different from a signal generated and provided to drive each other of the ultrasound piezoelectric elements, such that at least one of a frequency, a frequency content, an energy content and a transmission duration of ultrasound energy emitted from each of the ultrasound piezoelectric elements driven by a respective different signal is identifiably different.

3. The ultrasound flashlight (USFL) of claim 2, wherein the ultrasound energy emitted from each of the ultrasound piezoelectric elements is separately identifiable from each other of the ultrasound piezoelectric elements in the image that operates as the guide.

4. The ultrasound flashlight (USFL) of claim 1, wherein the image that operates as the guide is displayed on a display device that is connected directly to the connector, wherein the controller is connected to an ultrasound probe that is used to generate said image and wherein the controller processes ultrasound energy received via the ultrasound probe to generate said image.

5. The ultrasound flashlight (USFL) of claim 1, wherein the controller is attached to or integral with the insert.

6. The ultrasound flashlight (USFL) of claim 1, wherein the controller at a location that is remote from the insert.

7. The ultrasound flashlight (USFL) of claim 6, wherein the controller is part of an ultrasound imaging system.

8. The ultrasound flashlight (USFL) of claim 7, wherein the image that operates as the guide is displayed on a display device, and wherein the display device is part of the ultrasound imaging system.

9. The ultrasound flashlight (USFL) of claim 3, wherein the ultrasound energy emitted from each of the ultrasound piezoelectric elements that is presented in the image that operates as the guide is separately identifiable from the ultrasound energy emitted from each other of the ultrasound piezoelectric elements and presented in the image that operates as the guide, thereby identifying a different location of each communication port of the needle in said image.

10. The ultrasound flashlight (USFL) of claim 9, wherein the different locations of each communication port of the needle are identified by a different color in said image.

11. An ultrasound imaging system configured to generate and present an ultrasound image of a needle inserted in an animal body to deliver a treatment solution to a target structure location, where the image may be relied upon as a guide for supporting positioning a delivery end of the needle at the target structure location, the ultrasound imaging system comprising:

an ultrasound wand or probe;

a computer processor to which the ultrasound wand or probe is connected;

a display device connected to the computer processor;

a needle comprising a housing including a delivery end formed with a delivery opening for delivering the treatment solution, an access end opposite the delivery end, a lumen extending along a longitudinal axis of the needle housing between the access end and the delivery opening and one or more communication ports in the housing configured to pass ultrasound energy from inside the lumen to outside the lumen without passing the treatment solution; and an insert having a first end and a second end disposed substantially opposite the first end along a longitudinal axis of the insert, where the insert includes one or more ultrasound piezoelectric elements arranged proximate the first end and a connector positioned at the second end for connecting the piezoelectric elements to the computer processor;

wherein the insert is configured to be inserted into the access end of the needle so that each of the ultrasound piezoelectric elements aligns with a respective one of the communication ports of the needle;

wherein during USFL operation, ultrasound energy generated by the each of the ultrasound piezoelectric elements passes substantially unobstructed though each one of the communication ports aligned therewith; and wherein the generated ultrasound energy from the piezoelectric elements that passes through the communication ports is detected by the ultrasound probe or wand, processed by the computer processor and displayed on the display device in an image that operates as the guide for supporting the practitioner's positioning of the needle.

12. The ultrasound imaging system according to claim 11, further comprising a memory for storing computer code for generating signals used to drive the ultrasound piezoelectric elements, for controlling the ultrasound energy transmitted from the wand or probe in a transmit mode and for processing ultrasound energy received by the wand or probe in receive mode.

13. The ultrasound system according to claim 11, wherein the display device is positioned in the wand or probe.

14. The ultrasound system according to claim 13, wherein the computer processor is positioned in the wand or probe.

15. An ultrasound-based method for guiding a needle and insert combination in an animal body to deliver a treatment solution to a target structure location, wherein the needle comprises a housing with a delivery end formed with a delivery opening, an access end opposite the delivery end, a lumen extending along a longitudinal axis of the needle housing between the access end and the delivery opening and one or more communication ports in the housing configured to pass ultrasound energy from inside the lumen to outside the lumen without passing the treatment solution and wherein the insert comprises a first end and a second end disposed substantially opposite the first end along a longitudinal axis of the insert, one or more ultrasound piezoelectric elements arranged proximate the first end and a connector positioned at the second end for connecting the piezoelectric elements to control electronics, the method comprising the acts of:

first inserting the insert into the access end of the needle so that the one or more ultrasound piezoelectric elements are aligned with the one or more communication ports in the needle;

second inserting the needle and insert combination into the animal body;

operating the controller to generate and provide an electrical signal to each ultrasound piezoelectric element within the insert, whereby each ultrasound piezoelectric element generates and emits ultrasound energy through the respective communication ports in the needle to which said each ultrasound piezoelectric elements are aligned;

operating an ultrasound transducer or probe to receive at least the ultrasound energy emitted from the communication ports in the needle;

processing the received ultrasound energy and generating a display image that identifies a location of the needle and insert combination, a location of the target structure and a location of the communication ports; and guiding the needle and insert combination to the target structure in reliance upon the generated display image.

16. The method according to claim 15, wherein the step of processing the received ultrasound energy and generating the display image identifies the location of the communication ports using a different color for each target port location.

17. The method according to claim 15, wherein the step of processing the received ultrasound energy and generating the display image identifies the location of the communication ports using a different color for each communication port location.

18. The method according to claim 15, wherein the insert includes an ultrasound piezoelectric element at a tip end, and wherein the step of first inserting includes aligning the ultrasound piezoelectric element at the tip end with the delivery opening in the delivery end of the needle so that signal energy that is generated by said tip end ultrasound piezoelectric element is emitted out of the delivery end in a direction substantially aligned with the longitudinal axis of the insert.

19. The method according to claim 18, wherein the step of guiding includes generating and communicating a signal to the practitioner when the delivery end of needle and insert combination arrives at the target structure, in reliance upon the received ultrasound energy emitted from the delivery end thereof.

20. The method according to claim 15, wherein the target structure is a fetus or a tumor.

* * * * *